United States Patent [19]

Wuensch

[11] Patent Number: 4,503,716
[45] Date of Patent: Mar. 12, 1985

[54] MOLTEN METAL SAMPLER

[76] Inventor: Hartmut Wuensch, Eichendorffstr. 7, D4020 Mettmann, Fed. Rep. of Germany

[21] Appl. No.: 461,284

[22] Filed: Jan. 27, 1983

[30] Foreign Application Priority Data

Feb. 2, 1982 [DE] Fed. Rep. of Germany ....... 3203505

[51] Int. Cl.³ .............................................. G01N 1/12
[52] U.S. Cl. ................. 73/864.57; 73/864.58
[58] Field of Search ......... 73/864.57, 864.56, DIG. 9, 73/864.55, 864.53, 864.54, 864.58, 864.59; 249/DIG. 4

[56] References Cited

U.S. PATENT DOCUMENTS

| 3,583,236 | 6/1971 | Taylor | 73/DIG. 9 |
| 4,002,074 | 1/1977 | Collins | 73/864.57 |
| 4,048,857 | 9/1977 | Bardenheuer et al. | 73/864.56 X |
| 4,112,771 | 9/1978 | McDevitt | 73/864.57 |
| 4,116,070 | 9/1978 | Falk | 73/864.57 |
| 4,140,019 | 2/1979 | Falk | 73/864.57 |
| 4,291,585 | 9/1981 | Kolb et al. | 249/DIG. 4 |
| 4,317,380 | 3/1982 | Collins | 73/864.56 |

FOREIGN PATENT DOCUMENTS 2845566  4/1979  Fed. Rep. of Germany ... 73/864.57

Primary Examiner—Gerald Goldberg
Assistant Examiner—Tom Noland
Attorney, Agent, or Firm—Fuller, House & Hohenfeldt

[57] ABSTRACT

A molten metal sampler has a mold which forms a sampler with a disc portion for spectrographic analysis with a thinner skirt for punching pellets for combustion analysis. The skirt is positioned beneath the disc to afford floatation of impurities into the disc or a riser which communicates with the disc-forming recesses.

6 Claims, 6 Drawing Figures

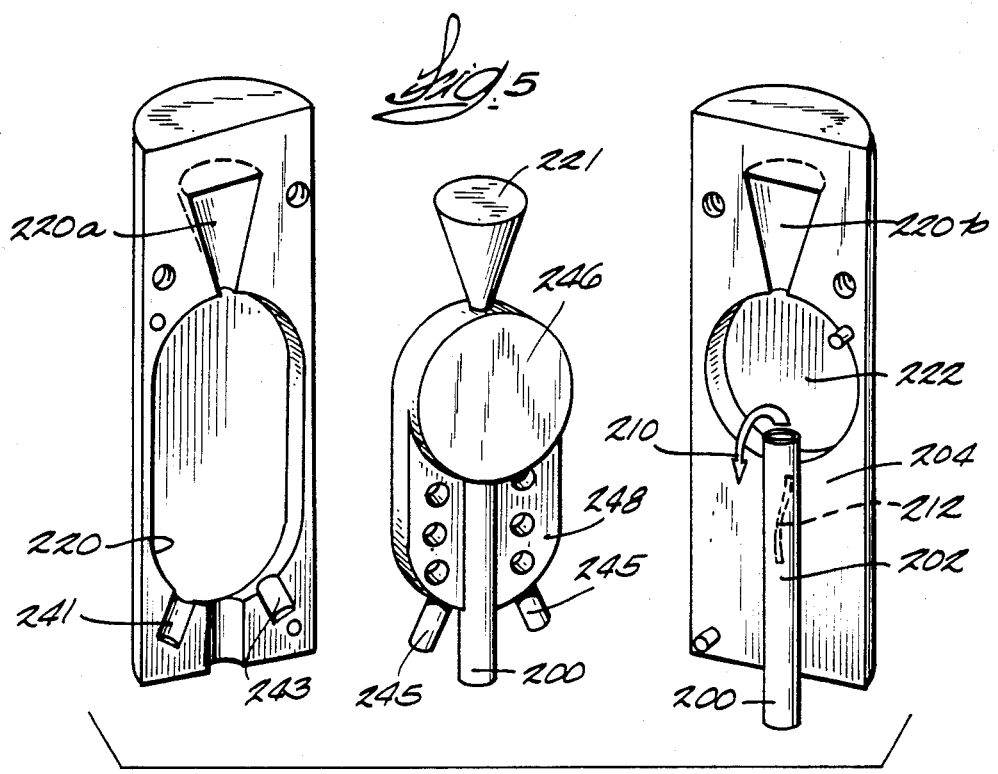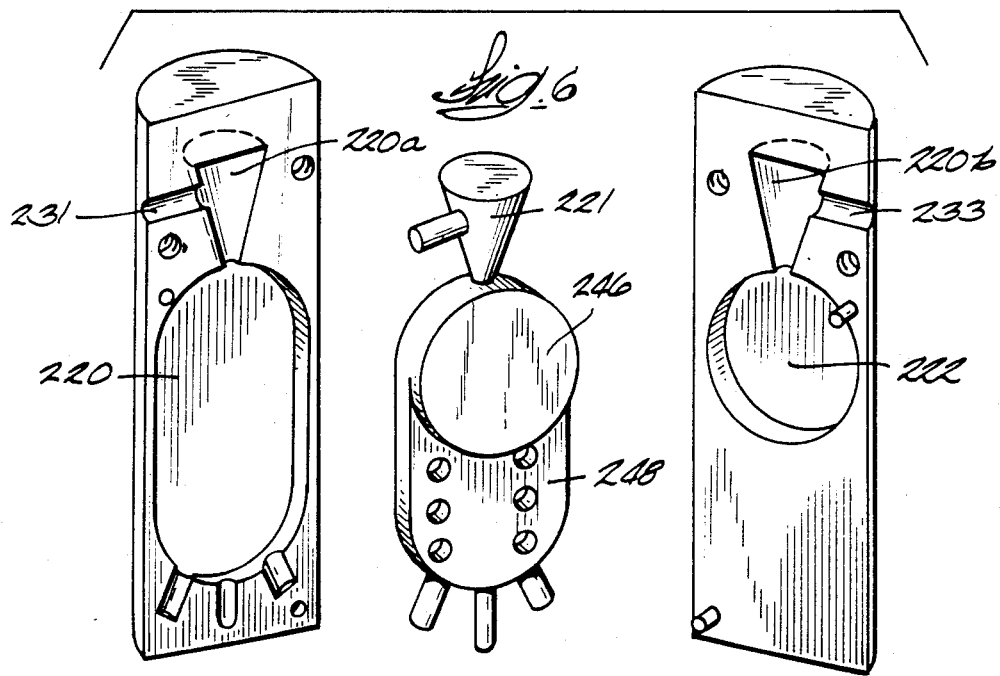

MOLTEN METAL SAMPLER

BACKGROUND OF THE INVENTION

The invention relates to molten metal samplers which retrieve a sample which is suitable for laboratory analysis to determine the content of the melt. Various types of samplers have been developed which form disc-shaped specimens and pin specimens. In addition, a sampler has been developed as illustrated in German laid-open specification No. 28 45 566, which shows a skirt projecting from a thicker sample portion which is suitable for punching out small pellets for later analysis. The pellets are particularly suitable for combustion analysis in an induction furnace. The sampler illustrated in the above German specification has been found to result in significant impurities in the peripheral skirt, and hence the test data is not as representative of the melt as desired. Furthermore, the skirt is difficult to clean preparatory to analysis and the punching of the pellets.

SUMMARY OF THE INVENTION

The invention provides a molten metal sampler which molds a sample having a relatively thick disc-shaped portion and, in addition, a thin skirt located below the disc portion when the sampler is oriented for obtaining a specimen. The skirt has one surface co-planar and co-extensive with one surface of the disc and provides an elongated surface which is readily machine cleaned prior to punching out pellets for combustion analysis. With the skirt located below the thicker disc, a large volume chamber is provided which enables impurities to float up in an unrestricted manner into the thicker portion to result in the skirt being a more representative sample of the melt than with the prior art sampler. In some embodiments, a riser cone located above the thicker disc portion provides increased volume for flotation of impurities from the skirt portion.

Further objects, features and advantages of the invention will become apparent from the disclosure.

DESCRIPTION OF THE DRAWINGS

FIG. 5 is an exploded perspective view of mold halves and a sample formed by the mold halves of a further embodiment of the invention.

FIG. 6 is an exploded view of a further modified embodiment of the invention.

DESCRIPTION OF THE PREFERRED EMBODIMENT

Although the disclosure hereof is detailed and exact to enable those skilled in the art to practice the invention, the physical embodiment herein disclosed merely exemplify the invention which may be embodied in other specific structure. The scope of the invention is defined in the claims appended hereto.

Figure 1:
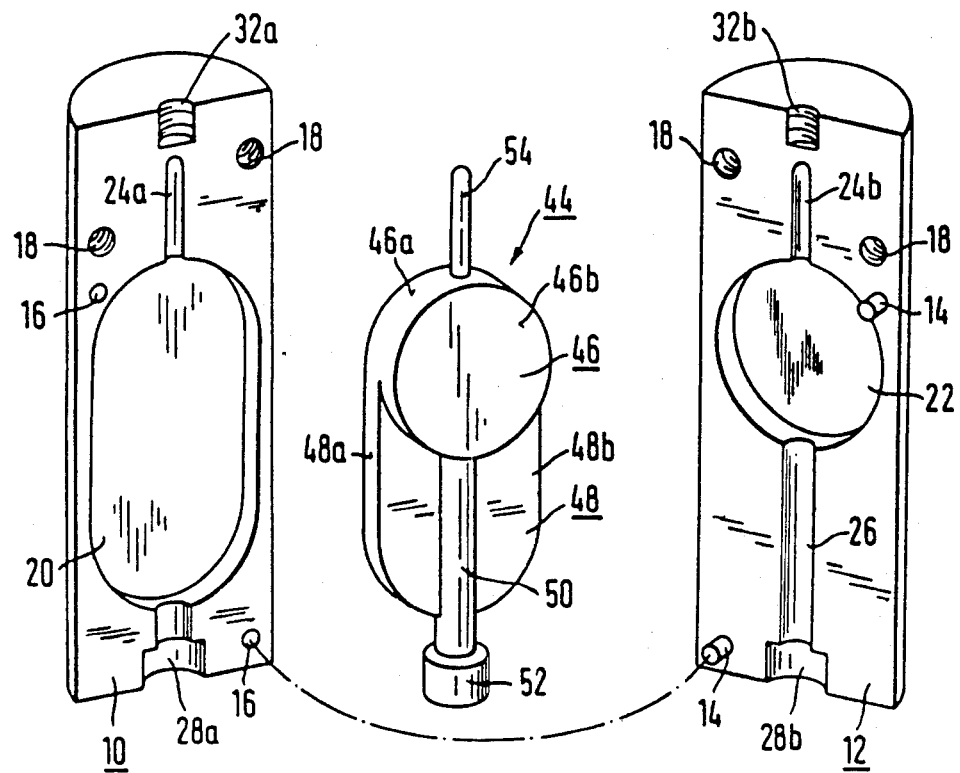
FIG. 1 is an exploded perspective view of two mold halves and the sample formed therein by the mold halves in accordance with the invention.

FIG. 1 illustrates two mold halves 10 and 12 which are assembled in proper relationship by pins 14 which are received in apertures 16. Screws threaded into threaded apertures 18 can be employed to secure the two metal mold halves together. Although the drawings illustrate metal mold halves which are reusable, ceramic or refractory consumable mold halves can be employed to accomplish the objectives of the invention and mold the samples illustrated in the drawings.

Mold half 10 has an elongated recess 20 which cooperates with a recess 22 to form the specimen or sample 44. At the upper end of the recesses 20, 22 are provided complementary grooves 24a and 24b which form a pin 54 as illustrated and also insure complete filling of the mold portions which form the disc 46. The mold fill passage includes recess 26 and recesses 28a and 28b. Recesses 20 and 26 cooperate to form sample portion 50 and recesses 28a and 28b cooperate to form sample portion 52.

Figure 2:
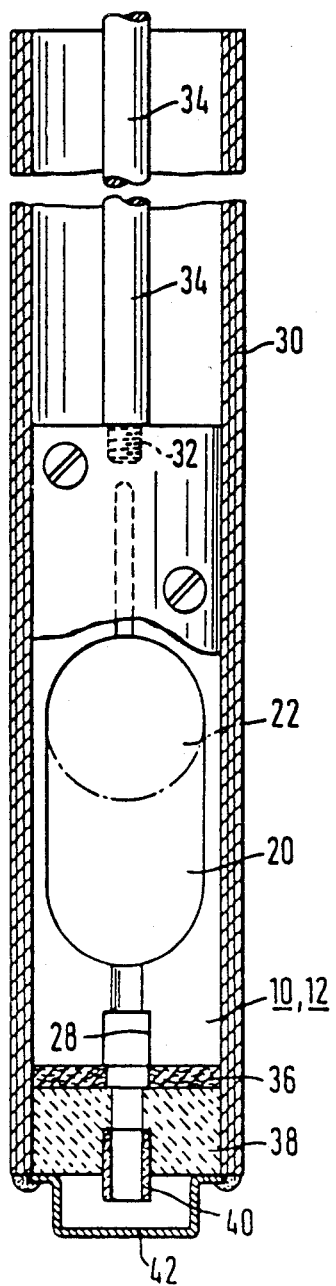
FIG. 2 is an elevation view showing the sample molds of FIG. 1 contained in a lance.

As illustrated in FIG. 2, the mold halves 10 and 12 are contained in a cardboard sleeve or tube 30 which is typically employed for protection of the mold for immersion of molten metal sampling equipment into the steel melt. A rod 34 having a threaded end 32 can be threadably received in threaded apertures 32a, 32b and can be employed for manipulating and immersing the sampler. Also illustrated in FIG. 2 is a packing or seal 36 of refractory fiber or heat-resistant material to protect the lower end of the metal mold halves 10 and 12. A refractory plug or disc 38 seals the bottom of the cardboard tube and can be cemented in place by refractory cement. A fused quartz fill tube 40 can be employed to provide a smooth passage into the mold cavity. A fusable cap 42 is typically employed to prevent entry of slag into the fill passage prior to adequate and deep penetration of the sampler into the melt below the slag layer. The sampler illustrated in FIGS. 1 and 2 is also suitable for use with a vacuum pump to cause filling of the sample into the sample cavity, as illustrated in various prior art pneumatic sampler patents.

After the sample is formed, small round pellets can be punched out of the skirt 48 after the planar sample surface formed along the elongated wall recess 20 is cleaned. The sample 44 has a disc portion 46 with an annular surface 46a, and a flat surface 46b and a skirt 48 with peripheral surface 48a and a flat surface 48b. The elongated surface which matches recess 20 can be readily cleaned by an abrasive belt or disc or the like. The surface 48b, however, is not easily cleaned because of the juncture of disc portion 46 and surface 48b. After the pellets are punched out, the skirt 48 is machined off the disc 46, which is then available for spectrographic or other forms of analysis. The pin 54 can also be used for combustion analysis.

Figure 3:
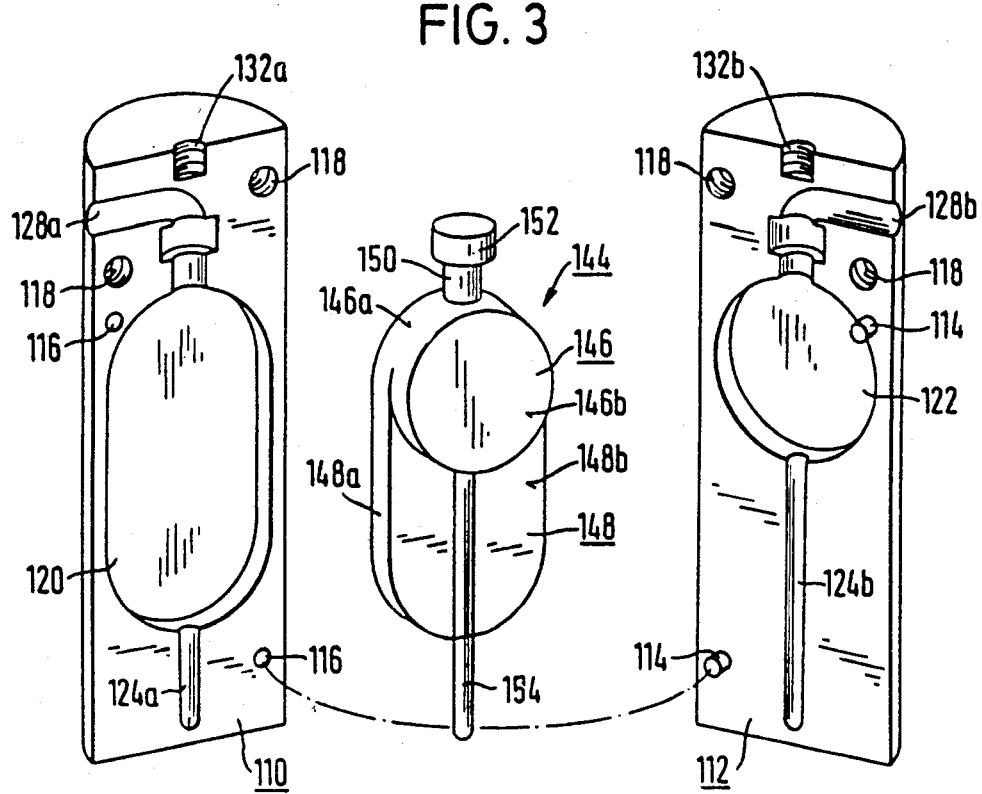
FIG. 3 is a modified embodiment in which the mold halves provide a side entry fill port.
Figure 4:
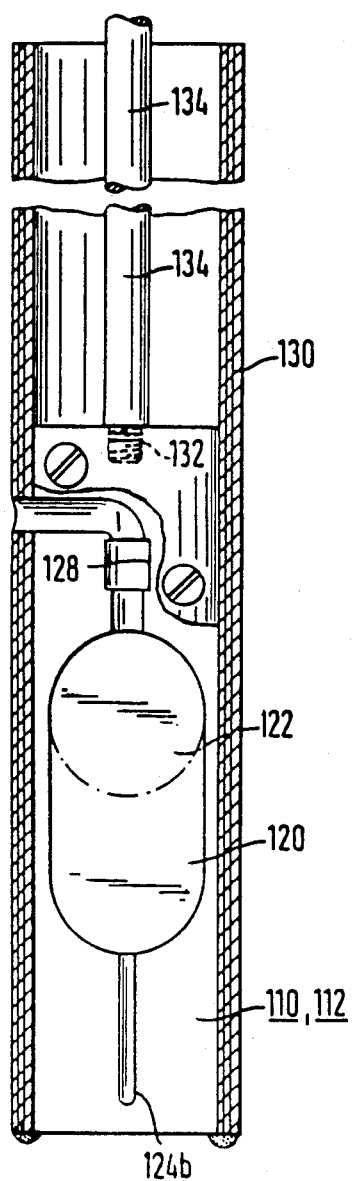
FIG. 4 is a view of the mold halves illustrated in FIG. 3 contained in a lance.

In FIGS. 3 and 4, the corresponding parts are identified with the same last two numbers but in the 100 number series. The fill passage is formed by grooves or recesses 128a and 128b which communicates with the recesses formed in the mold halves 110 and 112 to provide the sample 144.

In both samplers illustrated in FIGS. 1 and 3, the larger disc portion provides for convenient flotation of impurities away from the lower skirt to provide a more representative sample of the melt.

In the modified embodiment illustrated in FIG. 5, a fused quartz fill tube 200 is positioned in a recess 202 in mold half 204. Thus the molten metal will flow through the tube 200 during the filling operation and initially enter the recess 222 and then flow downwardly as indicated by arrow 210 to fill the recess 220 below the top of the fill tube 202. It has been found that this provides a skirt portion 248 which is a more representative sample. This is because the molten which initially flows into the mold cavity 222 consumes the oxygen in that recess and forms a shell in the recess 222, and thus the molten metal which flows downwardly to form the skirt has not been oxidized to the same extent as the initial flow of metal into recess 222. The fill passage 202 can also contain deoxidant or kill 212 which can be used to deoxidize the sample before it reaches any of the sample cavities. The tortuous flow path resulting from the spillover from the top of the tube 200 also mixes the sample and any kill that is used to make the skirt more uniform in composition.

The embodiment illustrated in FIG. 5 also includes semi-conical recesses 220a and 220b which cooperate to form a riser 221 at the top of the sample. The riser recesses afford increased volume above the skirt to enhance flotation of impurities away from the disc portion 246 and skirt 248.

In FIG. 5, the recess 220 is also provided with short pin recesses 241 and 243 to form pins 245 in the specimen. These pin samples will benefit from the advantageous flow path to provide representative samples.

In FIG. 6 there is illustrated a further embodiment in which recesses 220a and 220b are provided in the mold halves which also form part of the fill passage together with the recesses 231 and 233. Again, the riser cone affords space for flotation of impurities from the recesses 220 and 222.

In both FIGS. 5 and 6 the molded samples are illustrated with the pellets punched from the skirt portion. The elongated co-extensive-co-planar surface of the skirt 248 and disc 246 enable machine cleaning of at least one side of the skirt and hence pellets to greatly reduce the time for processing the samples prior to analysis. The use of the thin skirt enables machine punching of the pellets, whereas the thicker disc portions are conventionally sized for the standard spectrographic disc.

I claim:

1. A molten metal sampler including opposed mold halves, said mold halves including cooperating recesses to form a fill passage having a sample inlet and communicating with relatively thick disc sample portion recesses and a recess in one of said mold halves to form a relatively thin skirt sample portion extending from said disc sample portion toward said inlet so that when the sampler is in use the skirt portion recess will be filled prior to the disc portion, said skirt sample portion having at least one wall co-extensive and co-planar with said disc portion and being formed by a wall which extends continuously along one side of the disc portion and skirt portion.

2. The molten metal sampler of claim 1 including a fill tube extending through recesses in said opposed mold halves, said fill tube having an exit above the uppermost level of the skirt portion when the sampler is in use so as to initially introduce molten metal into the disc portion recess prior to the metal spilling over into the recess that forms the skirt portion.

3. The molten metal sampler of claim 1 wherein said recess forming said skirt portion and the recess in the one of said mold halves not including the skirt forming recess each includes a lower communicating recess when in use which forms a pin sample portion.

4. The molten metal sampler of claim 1 in which the skirt portion is below the disc portion when the sampler is in use to provide a relatively large volume for flotation of impurities upwardly from the skirt portion.

5. A molten metal sampler including opposed mold halves, said mold halves including cooperating recesses to form a relatively thick disc sample portion and a recess in one of said mold halves to form a relatively thin skirt sample portion extending from said disc sample portion, said skirt sample portion having at least one wall co-extensive and co-planar with said disc portion and being formed by a wall which extends continuously along one side of the disc portion and skirt portion and wherein said sampler includes opposed recesses in said mold half which form a conical riser portion to afford flotation of impurities from the disc portion and skirt portion.

6. The molten metal sampler of claim 5 in which said riser forming recesses communicate with a side fill passage and also the sample forming recesses to form a part of a sample inlet passage.

* * * * *